US010520298B2

(12) United States Patent
Chen et al.

(10) Patent No.: US 10,520,298 B2
(45) Date of Patent: Dec. 31, 2019

(54) STRUCTURAL DAMAGE DETECTION

(71) Applicant: BAE SYSTEMS plc, London (GB)

(72) Inventors: Jiye Chen, Portsmouth (GB); Heman Mamand, Portsmouth (GB)

(73) Assignee: BAE SYSTEMS PLC, London (GB)

(*) Notice: Subject to any disclaimer, the term of this patent is extended or adjusted under 35 U.S.C. 154(b) by 240 days.

(21) Appl. No.: 15/542,625

(22) PCT Filed: Jan. 12, 2016

(86) PCT No.: PCT/GB2016/050062
§ 371 (c)(1),
(2) Date: Jul. 10, 2017

(87) PCT Pub. No.: WO2016/113551
PCT Pub. Date: Jul. 21, 2016

(65) Prior Publication Data
US 2018/0266809 A1 Sep. 20, 2018

(30) Foreign Application Priority Data
Jan. 13, 2015 (GB) .................................. 1500496.3

(51) Int. Cl.
*G01B 11/16* (2006.01)
*G01M 5/00* (2006.01)
(Continued)

(52) U.S. Cl.
CPC ............ *G01B 11/16* (2013.01); *G01M 5/005* (2013.01); *G01M 5/0033* (2013.01);
(Continued)

(58) Field of Classification Search
CPC .. G01N 2021/8887; G01N 3/068; G01N 3/08; G01N 2203/0062; G01M 5/0091; G01M 5/0033; G01M 5/005
See application file for complete search history.

(56) References Cited

U.S. PATENT DOCUMENTS 5,726,907 A 3/1998 Davidson et al.

8,818,078 B2 * 8/2014 Telfer .................. F02C 1/00
382/154
(Continued)

FOREIGN PATENT DOCUMENTS

| CN | 102305795 A | 1/2012 |
| CN | 102359966 A | 2/2012 |
| WO | 2016113551 A1 | 7/2016 |

OTHER PUBLICATIONS

International Preliminary Report on Patentability received for Patent Application No. PCT/GB2016/050062, dated Jul. 27, 2017. 10 pages.
(Continued)

*Primary Examiner* — Judy Nguyen
*Assistant Examiner* — Leo T Hinze
(74) *Attorney, Agent, or Firm* — Finch & Maloney PLLC

(57) ABSTRACT

Disclosed is a method of assessing a structural defect presence in a structure, the method comprising the steps of: determining at least one critical damage strain value of the structure, capturing a first image of a surface of the structure under a first loading condition; capturing a second image of the surface of the structure under a second loading condition; assigning a position matrix on the captured first image; obtaining a deformation matrix comprising a deformation value at each position of the position matrix by using an image correlation technique on the first and second images, and by comparing deformation of corresponding parts of the surface captured therein; calculating a strain matrix using the obtained deformation matrix; and determining a micro-crack to be present at a position if an element of the strain matrix representing the strain at the position is greater than or equal to a predetermined critical damage strain value, wherein the critical damage strain value is a strain value at which a micro-crack is detected or predicted to appear and/or propagate.

18 Claims, 10 Drawing Sheets

(51) Int. Cl.
  *G01N 3/06* (2006.01)
  *G01N 3/08* (2006.01)
  *G01N 21/88* (2006.01)

(52) U.S. Cl.
  CPC .......... *G01M 5/0091* (2013.01); *G01N 3/068* (2013.01); *G01N 3/08* (2013.01); *G01N 2021/8887* (2013.01); *G01N 2203/0062* (2013.01)

(56) References Cited

U.S. PATENT DOCUMENTS

2011/0106459 A1   5/2011  Christ, Jr. et al.
2011/0316712 A1  12/2011  Mciver et al.
2013/0202192 A1   8/2013  Telfer et al.

OTHER PUBLICATIONS

International Search Report and Written Opinion received for Patent Application No. PCT/GB2016/050062, dated Mar. 17, 2016. 12 pages.
GB Intellectual Property Office Search Report under Section 17(5) received for GB Patent Application No. 1500496.3, dated Jun. 30, 2015. 3 pages.
Extended European Search Report issued for EP Patent Application No. 15275007.1, dated Jul. 16, 2015. 10 pages.
Dautriat, et al., "Localized deformation induced by heterogeneities in porous carbonate analysed by multi-scale digital image correlation," Elsevier, Tectonophysics 503 (2011) pp. 100-116.
Mouhmid, et al., An experimental analysis of fracture mechanisms of short glass fibre reinforced polyamide 6,6 (SGFR-PA66), Elsevier, Composites Science and Technology 69, (2009) pp. 2521-2526.

\* cited by examiner

STRUCTURAL DAMAGE DETECTION

The present invention concerns the provision of a method or an apparatus for assessing an effect of a loading on a structure.

Embodiments of the invention find particular, but not exclusive, use when a mechanical and/or thermal load is applied to a concrete structure which comprises a portion made from concrete. When such a mechanical and/or thermal load is applied to a concrete structure, structural damage such as a crack, both visible and invisible to the naked eye looking at an external surface of the structure, can occur. Such structural damage or crack can then lead to further structural defects eventually leading to structural instability.

For example, a crack in a reinforced concrete structure exposed to a cyclic or tidal exposure to sea water, i.e. those located in a costal or offshore regions, may allow ions in the sea water to enter the concrete structure and reach the reinforcing steel embedded in the concrete structure through the crack. This can then lead to corrosion of the reinforcing steel which, in turn, can reduce the cross sectional area of the steel, weaken the bonding between the steel and the concrete portion through expansion of the rust, and lower the strength of concrete portion. Such structural defects significantly worsen serviceability, durability and strength of the reinforced concreted structures.

It would be advantageous to be able to detect and/or predict such structural defects before they significantly affect the structural stability/integrity of the reinforced concrete structure. One such method is a non-destructive measurement technique using a digital image correlation. However, as the digital image correlation relies on the structural defects being visible on the outer surface of the structure, which also depends on the maximum resolution of the digital image correlation technique, it is unable to detect and/or predict many potentially fatal structural defects such as micro cracks before the structural stability/integrity has been compromised to an irreversible degree.

It is an aim of embodiments of the present invention to provide a method or an apparatus for assessing an effect of loading on a structure so that structural damage can be detected or predicted using the method or the apparatus.

According to the present invention there is provided a method and apparatus as set forth below and in the appended claims. Other features of the invention will be apparent from the dependent claims, and the description which follows.

According to a first aspect of the invention, there is provided a method of assessing a structural defect presence in a structure, the method comprising the steps of:

determining at least one critical damage strain value of the structure, capturing a first image of a surface of the structure under a first loading condition;

capturing a second image of the surface of the structure under a second loading condition;

assigning a position matrix on the captured first image;

obtaining a deformation matrix comprising a deformation value at each position of the position matrix by using an image correlation technique on the first and second images, and by comparing deformation of corresponding parts of the surface captured therein;

calculating a strain matrix using the obtained deformation matrix; and determining a micro-crack to be present at a position if an element of the strain matrix representing the strain at the position is greater than or equal to a predetermined critical damage strain value, wherein the critical damage strain value is a strain value at which a micro-crack is detected or predicted to appear and/or propagate.

Suitably, the structure comprises a portion made of heterogeneous material. Suitably, the structure comprises a concrete portion.

Suitably, the position matrix, deformation matrix, and/or strain matrix are assigned/obtained/calculated for only a portion of the captured first or second image.

Suitably the deformation matrix comprises elements representing a displacement of each position of the position matrix.

Suitably, the strain matrix comprises an element representing a material property related to crack occurrence and/or propagation. Preferably, the strain matrix comprises an element representing a strain value at each position. Alternatively, the strain matrix comprises an element representing a stress value at each position.

Suitably, the first and second loading conditions comprise an equivalent physical loading quantity but the second image is captured at a different time from the time of capturing the first image.

Suitably, the first image of the structure is captured when the structure is under a first loading. Then after a predetermined time has passed, the second image is captured with the equivalent loading as the loading first loading.

Suitably, the first and second loading conditions comprise a different physical loading quantity from one another.

Suitably, the first loading condition comprises a loading experienced by the structure when the structure is under its normal working condition with no external load applied thereto; and the second loading condition comprises a loading experienced by the structure when the structure is under an external load applied thereto.

Suitably, an external load is a load applied to the structure by a mass that is not a part of the structure, for example not an integral and/or permanent part of the structure. Suitably, under its normal working condition the structure may engage a separate mass which engages the structure for a period of time, and the first loading comprises the load and/or weight applied to the structure by the separate mass.

Suitably, the first loading condition comprises a loading experienced by the structure when the structure is under an external load of a predetermined value other than zero; and the second loading condition comprises a loading experienced by the structure when the structure is under an external load of a different non-zero value than the predetermined value.

Suitably, the method further comprises a step of capturing a third image of the surface of the structure under a third loading condition, wherein the obtaining the deformation matrix, the calculating the strain matrix and the determining a micro-crack to be present at a position further comprise obtaining a deformation value at each position of the position matrix using an image correlation technique on the third image with at least one of the first or second images.

Suitably, the obtaining the deformation matrix, the calculating the strain matrix and the determining a micro-crack to be present at a position comprise averaging and/or interpolating from the deformation values and/or strain values obtained/calculated from the first and second image comparison, the first and third image comparison, and/or the second and third image comparison.

Suitably, the third loading condition is the same as the first or second loading condition, and the averaging comprises averaging the deformation values and/or strain values obtained/calculated from the first or second image under the same loading condition as the third loading condition.

Suitably, the third loading condition is different from the first or second loading condition, and the interpolating comprises interpolating from the deformation values and/or strain values obtained/calculated from the first or second image under the different loading condition than the third loading condition.

Suitably, the method further comprises a step of applying or affixing an indicator on a part of the surface so that the indicator is detectable from the captured first, second or third image, whereby the part can be identified in the first, second or third image using the indicator.

Suitably, the indicator is a coating of detectable material, such as a paint. Suitably, the indicator is applied to the whole or at least a portion of the surface so that a surface defect such as a crack can be detected from a captured image of the surface more easily.

Suitably, the loading, first, second or third loading condition comprises a mechanical loading and/or a thermal loading.

Suitably, the mechanical loading comprises a dynamic loading of an external mass such as sea water, a static loading of a mass such as the mass of the structure itself and/or a changeable loading of a separate mass which engages the structure in normal use.

Suitably, the method determines/predicts a crack propagation path within the structure and/or the concrete portion. Suitably, the crack propagation path comprises at least two determined crack locations, wherein a crack location is a position determined to have a micro-crack present.

Suitably, the method further comprises a step of determining and/or detecting a crack propagation path comprising the sub-steps of:

determining a potential damage zone which is a set of all the neighbouring positions determined to have a micro-crack present;

obtaining a potential damage strain matrix by selecting the elements relating to the potential damage zone from the strain matrix;

determining at least one local maximum strain value for each row and/or column of the potential damage strain matrix if an element therein represents a strain with greater value than both the previous and subsequent elements in the potential damage strain matrix; and determining the crack propagation path to be a collection of positions related to the at least one local maximum strain values.

Suitably, the positions related to the at least one local maximum strain values is obtained by selecting the elements relating to the at least one local maximum strain values from the position matrix. Suitably, the crack propagation path comprises a collection of the positions related to the at least one local maximum strain values which only comprises positions related to local maximum strain values which are next to one another, either in the column-wise and/or row-wise direction of the potential damage strain matrix. Suitably, the crack propagation path comprises more than one collection of the positions related to the at least one local maximum strain values.

Suitably, a macro-crack is detectable from a single image when the crack is visible to the human eye from the single image and/or detectable using a digital image recognition technique from the single image.

Suitably, the critical damage strain value is a critical strain value at which a crack is likely to occur. Suitably, the determining the at least one critical damage strain value of the structure comprises the sub-steps of:

capturing a prior image before a detectable macro-crack has occurred;

capturing a post image after the detectable macro-crack has occurred;

setting the critical damage strain value as a first predicted critical strain value;

performing at least some of the rest of the method steps using the prior image as the first image, the post image as the second image and the first predicted critical strain value as the critical damage strain value, to determine a position with a micro-crack present; and performing the following sub-step at least once until there is an acceptable degree of correlation between the determined position and the location of the detectable macro-crack in the post image, wherein if there is an acceptable degree of correlation, saving the first predicted critical strain value as the determined critical damage strain value, and if there is not an acceptable degree of correlation, repeating at least some of the sub-steps for the determining at least one critical damage strain value after setting a second predicted critical strain value, which is different from the first predicted critical strain value, as the critical damage strain value.

Suitably, the method further comprises a step of determining and/or detecting a crack propagation path as discussed above, and the determining the at least one critical damage strain value of the structure comprise the sub-steps of:

capturing a prior image before a detectable macro-crack has occurred;

capturing a post image after the detectable macro-crack has occurred;

setting the critical damage strain value as a first predicted critical strain value;

performing at least some of the rest of the method steps using the prior image as the first image, the post image as the second image and the first predicted critical strain value as the critical damage strain value, to determine the crack propagation path; and performing the following sub-step at least once until there is an acceptable degree of correlation between the determined crack propagation path and the location of the detectable macro-crack in the post image, wherein if there is an acceptable degree of correlation, saving the first predicted critical strain value as the determined critical damage strain value, and if there is not an acceptable degree of correlation, repeating at least some of the sub-steps for the determining at least one critical damage strain value after setting a second predicted critical strain value, which is different from the first predicted critical strain value, as the critical damage strain value.

Suitably, there is an acceptable degree of correlation between the determined crack propagation path and the location of the detectable macro-crack in the post or second image when the determined crack propagation path comprises the location of the detectable macro-crack.

Suitably, there is an acceptable degree of correlation between the determined crack propagation path and the location of the detectable macro-crack in the post or second image when the detectable macro-crack is near a periphery of the determined crack propagation path.

Suitably, the saved critical strain value is used as a threshold value for determining a location and/or crack propagation path of a micro-crack resulting from the loading on the structure. Suitably, the first and/or second predicted critical strain value is obtained through a standard material test, such as ASTM (American Society for Testing and Materials) tensile test, performed on a sample which represents the structure and/or a composition material wherefrom the structure is made. Suitably, the second predicted critical strain value is extrapolated and/or interpolated from two different predicted critical strain values which did not show the acceptable degree of correlation from previous sub-steps for predicting or determining the critical damage strain value.

Suitably, the digital image correlation technique is used with the step for predicting or determining the critical strain damage value as described herein.

According to a second aspect of the invention, there is provided an assessment apparatus for assessing a structural defect presence in a structure, the apparatus comprising:

a communication unit configured to receive first data relating to a first image of a surface of the structure under a first loading condition, and to receive second data relating to a second image of the surface of the structure under a second loading condition; and a processor configured to:

determine at least one critical damage strain value of the structure;

assign a position matrix on the captured first image;

obtain a deformation matrix comprising a deformation value at each position of the position matrix by using an image correlation technique on the first and second images, and by comparing deformation of corresponding parts of the surface captured therein;

calculate a strain matrix using the obtained deformation matrix; and determine a micro-crack to be present at a position if an element of the strain matrix representing the strain at the position is greater than or equal to a predetermined critical damage strain value, wherein the critical damage strain value is a strain value at which a micro-crack is detected or predicted to appear and/or propagate.

Suitably, the communication unit is configured to receive the first and/or second data from an image capturing unit using a wired and/or wireless communication. Suitably, the communication unit is configured to receive the first data from a first image capturing unit and the second data from a second image capturing unit.

Suitably, the assessment apparatus further comprises an image capturing unit configured to capture the first image of at least a portion of the surface of the structure under the first loading condition, and to capture the second image of the at least the portion of the surface of the structure under the second loading condition.

Suitably, the image capturing unit is configured to capture the second image at a different time from the time of capturing the first image. Suitably, the temporal positions are measured from the initial application of the first and/or second loadings on the structure.

Suitably, the image capturing unit is configured to capture a plurality of images over a period of time, for example a moving picture, whereby data relating to a plurality of images is obtained. Suitably, the processor is configured to obtain the deformation matrix using the plurality of images.

Suitably, the assessment apparatus is configured to operate the method according to the first aspect of the invention.

According to a third aspect of the invention, there is provided a computer readable medium storing a computer program to operate the method according to the first aspect of the invention.

For a better understanding of the invention, and to show how embodiments of the same may be carried into effect, reference will now be made, by way of example, to the accompanying diagrammatic drawings in which.

Figure 1:
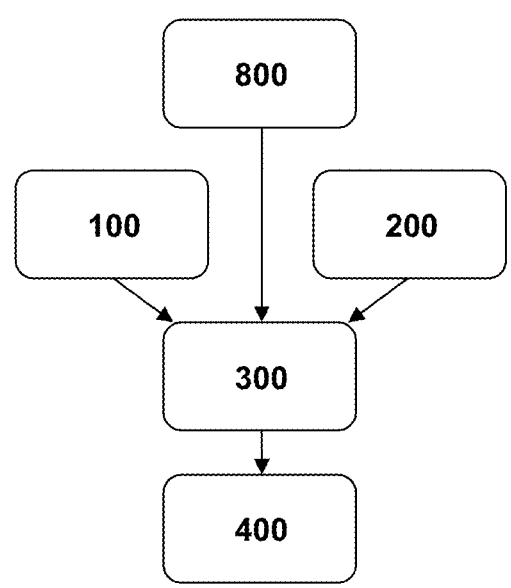
FIG. 1 shows a flowchart for performing an embodiment of the present invention.

For the purpose of this application, a macro-crack is a crack and/or a separation of the structure on a surface of the concrete structure which can be visibly detected from a captured image of the surface either by the human eye or using the digital image correlation technique. So a macro-crack is detectable from a single image when the crack is visible to the human eye from the single image and/or detectable using a digital image recognition technique from the single image. A micro-crack is a crack and/or a separation of the structure on a surface and/or inside the concrete structure, which cannot be visibly detected from a captured image of the surface either by the human eye or using the digital image correlation technique. For example, the macro-crack might be in the millimetre scale and the micro-crack might be in the micrometre scale.

It is understood that the detectability of the macro-crack and/or micro-crack, and the relevant quantitative scale thereof will depend on a number of factors such as the digital image recognition and/or correlation technique used on the image of the surface.

In general, the structural stability/integrity is irreversibly, or at least significantly, compromised once a macro-crack has occurred. Also, a presence of a micro-crack and the propagation thereof tends to lead to an occurrence of the macro-crack if no action is taken to treat the affected region of the structure.

The present invention aims to exploit this relationship between the macro-cracks and the micro-cracks to predict potential locations and/or propagation of the macro-cracks by detecting the locations and/or propagation of the micro-cracks. This then enables treatment, such as providing an additional concrete layer and/or reinforcement, of the structure before it suffers the irreversible/significant damage/structural defect. Also, this enables determination of whether the structure is still capable of dealing with the normal use loading condition and/or for how long the structure might remain safe to be used in the normal use loading condition. This determination then enables a repair, replacement and/or removal of the structural, and/or adjustment of the normal use loading condition, to be performed as appropriate.

For example, a structure such as a concrete beam without reinforcements can experience a 25% reduction in bending strength due to macro- and/or micro-cracks. This concrete beam will then be dangerous for use under the normal loading condition, i.e. the normal service condition. Even if the concrete beam is only subjected to micro-cracks leading to a 10% reduction in bending strength, it could be unsafe, in particular, under repeated cyclic loading conditions of sea water for example. Such beams with reduced bending strength need to be repaired and/or replaced. By predicting potential locations and/or propagation of the macro-cracks through detecting the locations and/or propagation of the micro-cracks, a vulnerable area of the structure with macro- and/or micro cracks is detected so that a scheme for repairing and/or replacing the affected and/or damaged structure, i.e. beam, can be implemented.

In FIG. 1, a method of assessing a structural defect presence in a structure is shown. The structure comprises a concrete portion which may experience such a structural defect under a loading condition.

For the purpose of the present invention, a concrete portion is chosen because concrete is a heterogeneous material wherein cracks appearing therein may be modelled at different scales. However, the brittle nature of concrete means any cracks appearing in a structure/portion made there-from is unlikely to propagate progressively and, therefore, may lead to detrimental effect on the structural stability/integrity without much visible/detectable warning. This makes concrete a good material for exploiting the aforementioned relationship between the macro-cracks and the micro-cracks to predict potential locations and/or propagation of the macro-cracks by detecting the locations and/or propagation of the micro-cracks.

However, it is understood that the method is applicable to a structure which comprises a portion made of any other material susceptible to experiencing a structural defect such as a crack, which can affect the structure and/or the portion's structural stability/integrity.

At step 800, the method determines at least one critical damage strain value of the structure. The at least one critical damage strain value may be determined by obtaining and/or receiving the at least one critical damage strain value from an apparatus for determining and/or storing critical damage strain values.

According to an embodiment, when the step 800 is performed, at least one arbitrary value is set as the at least one critical damage strain value. Alternatively, when the step 800 is performed, the at least one critical damage strain value is obtained from a standard material test such as ASTM (American Society for Testing and Materials) tensile test, which is performed on a sample which represents the structure and/or a composition material where from the structure is made.

The critical damage strain value is a strain value at which a micro-crack is likely or predicted to occur, appear and/or propagate. So the critical damage strain value can be used to compare with a particular strain value at a particular position or location to determine whether a micro-crack is likely to be present and/or propagate towards the particular position or location.

Further details on how such critical damage strain values may be determined for a particular structure is provided later in relation to steps shown in FIG. 7. According to an embodiment, the method of determining and/or storing critical damage strain values comprises the steps shown in FIG. 7 which are performed to determine at least one critical damage strain value for a particular given structure.

At step 100, first image data is obtained from a first image of a surface of the structure under a first loading condition. At step 200, second image data is obtained from a second image of the same surface of the structure under a second loading condition. How the first and/or second image data may be obtained is provided in more detail later in relation to FIGS. 2A and 2B.

A loading, first or second loading condition comprises a mechanical loading and/or a thermal loading. For example, the mechanical loading may be a dynamic loading of an external mass such as sea water on the structure, a static loading of a mass such as the mass of the structure itself and/or a changeable loading of a separate mass which engages the structure in normal use. The thermal loading may be different temperatures the structure might experience over its working life. Such temperature changes may then lead to thermal expansion and/or contraction of at least a part of the structure can result in an occurrence of a structural defect.

According to an embodiment, the first image of the structure is captured when the structure is under a first loading. Then after a predetermined time has passed, the second image is captured with the equivalent loading as the first loading. So the first and second loading conditions comprise an equivalent physical loading quantity, such as the same weight being placed on the structure, whilst the second image is captured at a different time from the time of capturing the first image. In this case, the time may be measured from the initial application of the weight on the structure. This enables the method to assess the crack presence and/or propagation over a period of time under the same loading condition which can be useful for assessing risks over a prolonged period of time.

According to another embodiment, the first image of the structure is captured when the structure is under a first loading. Then after a predetermined time has passed, the second image is captured with a second loading that is different from the first loading, i.e. the weight placed on the structure when the first image is captured is different from the weight placed on the structure when the second image is captured. So the first and second loading conditions comprise different physical loading quantities from one another. This enables the method to assess the crack presence and/or propagation under different loading conditions which can be useful for assessing risks in environments where the loading is likely to change.

According to yet another embodiment, both the physical loading quantity and the capture time of the first and second image are varied. This enables the method to assess the crack presence and/or propagation under different loading conditions over time, for example a structure exposed to a cyclic loading applied by sea water.

According to an embodiment, the first loading condition comprises a loading experienced by the structure when the structure is under its normal working condition with no external load applied thereto, and the second loading condition comprises a loading experienced by the structure when the structure has an external load applied thereto. The external load is a load applied to the structure by a mass that is not a part of the structure, for example not an integral and/or permanent part of the structure. So under its normal working condition the structure may not engage a separate mass, which may then engage the structure for a period of time. When the separate mass engages the structure, the structure experiences the second loading which comprises the load and/or weight applied to the structure by the separate mass. For example, the structure is a concrete beam on a bridge and the loading under the first loading condition is experienced when there is no vehicle travelling on the bridge. The loading under the second loading condition is then experienced when at least one vehicle is travelling on the bridge in the form of the weight of the at least one vehicle.

According to another embodiment, the first loading condition comprises a loading experienced by the structure when the structure is under an external load of a predetermined value other than zero, and the second loading condition comprises a loading experienced by the structure when the structure is under an external load of a different non-zero value than the predetermined value. This enables the method to make assessments when the structure is exposed to an external load all the time but at different quantities.

At step 300, the method obtains a deformation matrix comprising a deformation value from the first and second image data obtained in steps 100 and 200. An image correlation technique is used to process the first and second images and/or the first and second image data obtained at steps 100 and 200. The image correlation technique correlates portions of the first and second images as being the same part of the same surface of the structure so that comparison between correlated parts of the surface captured in the first and second images can be made. Further details on how the deformation matrix is obtained is provided later in relation to FIG. 3.

At step 400, a determination is made on whether a micro-crack is present at a particular position or not based on a predetermined critical damage strain value chosen from the at least one critical damage strain values determined at step 800. Further details on how the micro-crack presence determination is made is provided later in relation to FIG. 4.

Figure 2A:
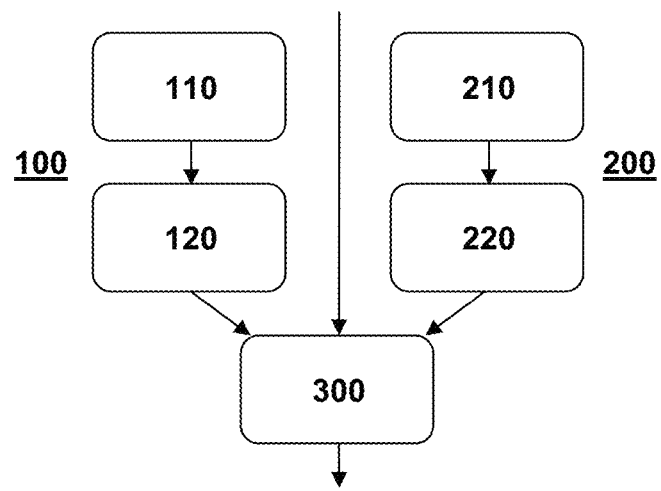
FIG. 2A shows a partial flowchart for performing an embodiment of the present invention with additional steps for receiving first and/or second image data.

FIG. 2A shows a partial flowchart for performing an embodiment of the present invention with additional steps for obtaining or receiving first and/or second image data.

The step 100 of obtaining first image data comprises a step 110 of capturing a first image of a surface of the structure under a first loading condition, and a step 120 of processing the captured first image to obtain the first image data. The step 200 of obtaining second image data comprises a step 210 of capturing a second image of the surface of the structure under a second loading condition, and a step 220 of processing the captured second image to obtain the second image data.

The first and second image data comprise information about features present on the captured surface. The features present may be colour, contrast, shape, and/or any entity that represents a characteristic of the surface, and the information about the features may be a grey scale value or any value indicative of the features, which can be used to distinguish a region of the surface from another region of the surface.

The obtained first and second image data are then used in step 300 to obtain a deformation matrix.

Figure 2B:
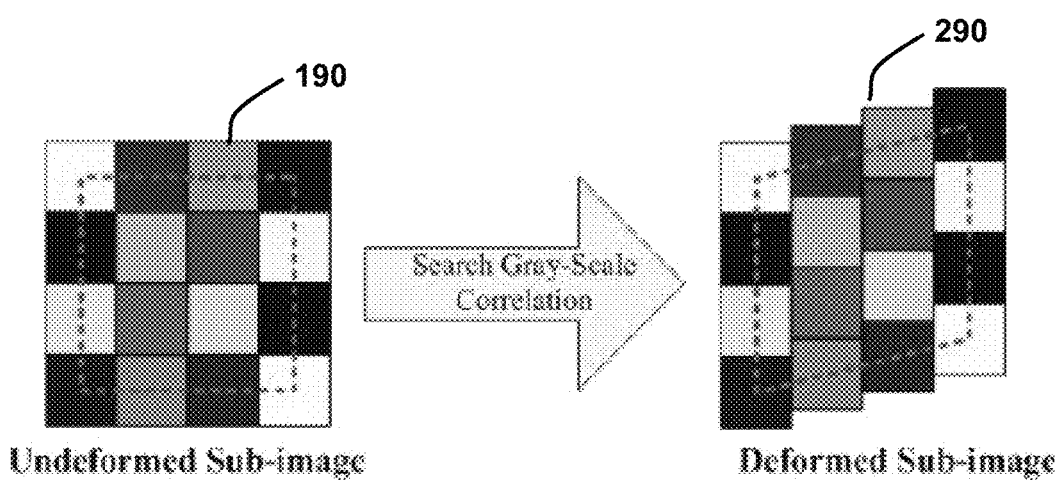
FIG. 2B shows an exemplary grey scale digital image correlation technique being used on images before and after deformation.

FIG. 2B shows an exemplary grey scale digital image correlation technique being used on images before and after a deformation so that the deformation matrix can be obtained at step 300.

The captured first and second images comprise regions with different colour and/or contrast so that the first and second image data obtained there-from comprise different grey scale values related to the regions. The grey scale values in the first image data obtained from the first image 190 captured before the deformation is compared with the grey scale values in the second image data from the second image 290 captured after the deformation to correlate each region in the first image 190 with its equivalent region in the second image 290.

According to an embodiment, the method further comprises a step of applying and/or affixing an indicator on the surface so that the indicator is detectable from the captured image, for example the first or second image. The indicator then enables the part or the region to be identified in the image using the indicator. For example, as an indicator comprising a coating of detectable material, such as paint could be used. The indicator, or the paint, can be applied to the whole or at least a portion of the surface so that a region and/or a surface defect such as a crack can be detected from a captured image of the surface more easily using the digital image correlation technique.

It is understood that any image correlation technique capable of distinguishing a region of the surface from another, and also capable of correlating the region with another region from a different image of the same surface could be used to achieve the same effect. As long as such distinction is possible and the distinguished regions from the first image can be correlated with the distinguished regions from the second image, the image correlation technique thereof can be used on the images to obtain the deformation matrix at step 300.

Figure 3:
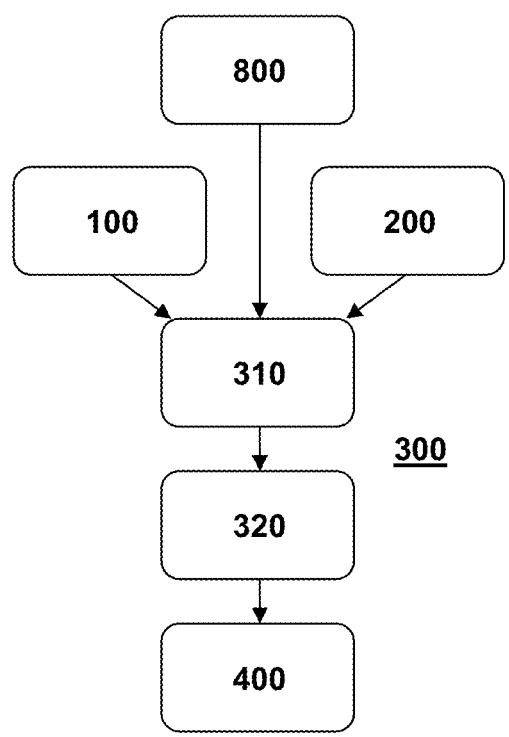
FIG. 3 shows a flowchart for performing an embodiment of the present invention with additional steps for obtaining a deformation matrix.

FIG. 3 shows a flowchart for performing an embodiment of the present invention with additional steps for obtaining a deformation matrix, i.e. step 300.

The step 300 comprises a step 310 of assigning a position matrix on the captured first image, and a step 320 of obtaining a deformation matrix using the assigned position matrix.

The step 310 of assigning a position matrix comprises assigning a grid and/or coordinate system to the first image so that each location or position therein can be identified using the position matrix. It is understood that any other system of identifying a location or a position may be used but for the purpose of the present invention use of a 2-dimensional coordinate system (x,y) is described herein.

The step 320 of obtaining a deformation matrix comprises using an image correlation technique to correlate different regions in the first image with the different regions in the second image. The deformation value can then be calculated by considering the change in the location or position of the correlated regions in the first and second images.

The deformation matrix comprises the calculated deformation value at each location or position of the surface. So the deformation value is obtained using an image correlation technique, such as that described in relation to FIG. 2B, on the first and second images. By comparing the location, position and/or partial surface area of the location, i.e. deformation, of the corresponding correlated regions or parts of the surface, a change in the location, position and/or surface area can be calculated, and the deformation value at the location or position is obtained.

According to an embodiment, the position matrix, the deformation matrix, and/or strain matrix are assigned/obtained/calculated for only a portion of the captured first or second image. This portion of the captured first or second image is a portion of the surface that represents a region of particular interest. This region of particular interest may be chosen based on its position within the surface. For example, a region that is positioned near an edge, which is likely to experience a high strain and/or stress, is chosen since a crack is more likely to appear in such a region.

According to an embodiment, a deformation value is a displacement of a region or part in the surface, and the deformation matrix comprises elements representing displacement at each position according to the assigned position matrix of the first image. The displacement is calculated from the position change of the corresponding correlated region or part between the first and second images. For example, the displacement at each location or position is represented by (u(x,y), v(x,y)), wherein u(x,y) and v(x,y) are displacement functions at coordinate (x,y) in x and y axis respectively. Then the deformation value of the deformation matrix is used to calculate a strain matrix which is used to determine a presence of a micro-crack at step 400.

Figure 4:
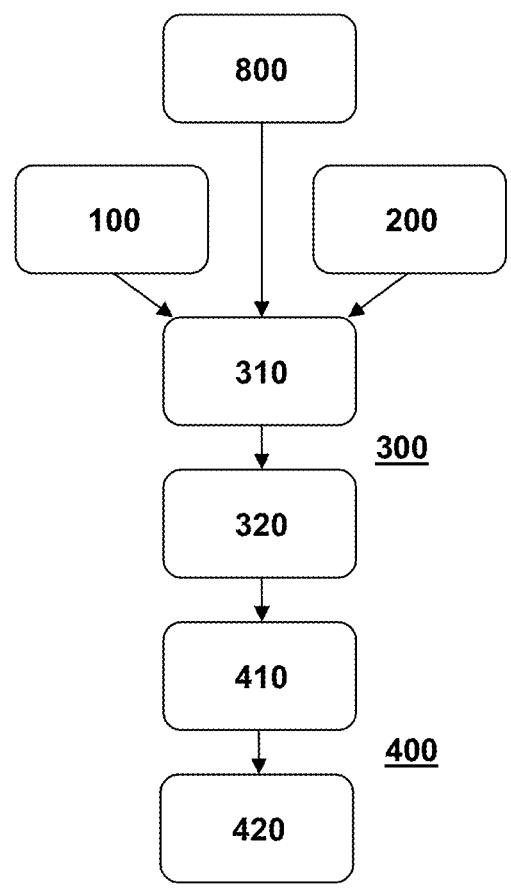
FIG. 4 shows a flowchart for performing an embodiment of the present invention with additional steps for determining a micro-crack presence.

FIG. 4 shows a flowchart for performing an embodiment of the present invention with additional steps for determining a micro-crack presence, i.e. step 400.

The step 400 comprises a step 410 of calculating a strain matrix using the obtained deformation matrix, and a step 420 of determining a micro-crack to be present at a position if an element of the strain matrix representing the strain at the position is greater than or equal to a predetermined critical damage strain value.

According to an embodiment, the strain matrix comprises an element representing a material property related to crack occurrence and/or propagation. Preferably, the strain matrix comprises an element representing a strain value at each position. So the strain matrix comprises a strain value at each location or position of the surface as an element.

A strain value in the strain matrix is calculated from the displacement in the deformation matrix and the assigned position matrix of the first image. The strain value is calculated for each region or part of the surface that is distinctively identifiable using the assigned position matrix. For example, if $$\varepsilon_{xx} = \frac{du}{dx} = \frac{u_{t2} - u_{t1}}{\Delta x_{t1}},$$

$$\varepsilon_{yy} = \frac{dv}{dy} = \frac{v_{t2} - v_{t1}}{\Delta y_{t1}}, \text{ and } \varepsilon_{xy} = \frac{du}{dy} + \frac{dv}{dx} = \frac{u_{t2} - u_{t1}}{\Delta y_{t1}} + \frac{v_{t2} - v_{t1}}{\Delta x_{t1}}$$

are normal strain in x-axis, normal strain in y-axis and shear strain respectively, the calculated strain values for the strain matrix may be a maximum principal strain at each location or position, $$\varepsilon_{max} = \frac{\varepsilon_{xx} + \varepsilon_{yy}}{2} + \sqrt{\frac{(\varepsilon_{xx} - \varepsilon_{yy})^2}{4}} + \varepsilon_{xy},$$

wherein $\Delta x_{t1}$ and $\Delta y_{t1}$ are lengths in x-axis and y-axis under t1 respectively, and $(u_{t1}, v_{t1})$ and $(u_{t2}, v_{t2})$ are displacement values under t1 and t2 condition respectively.

The t1 and t2 can be used to indicate the time when the relevant image was captured. So if the first image was captured under the first loading condition at time t1 and the second image was captured under the second loading condition at time t2, the t1 and t2 notation can be used to indicate both different loading conditions as well as temporally different positions. As long as there was a deformation between the capturing of the first and second images, and this deformation results in non-zero displacement values in at least one of $(u_{t1}, v_{t1})$ and $(u_{t2}, v_{t2})$, the strain matrix can be calculated.

According to another embodiment, the strain matrix comprises an element representing a stress value at each position and each determination, calculation, prediction, and/or detection step of the method can be performed based on a stress value. It is understood that any parameter that is related to and/or can affect the occurrence and/or propagation of a crack may be used as an element of the strain matrix. Examples of such a parameter might be stress or strain/stress energy values. It is also understood that use of such alternative parameter may involve conversion of the calculated strain value and/or matrix into the alternative parameter using a predetermined material property before the determination, calculation, prediction, and/or detection step.

Figure 5:
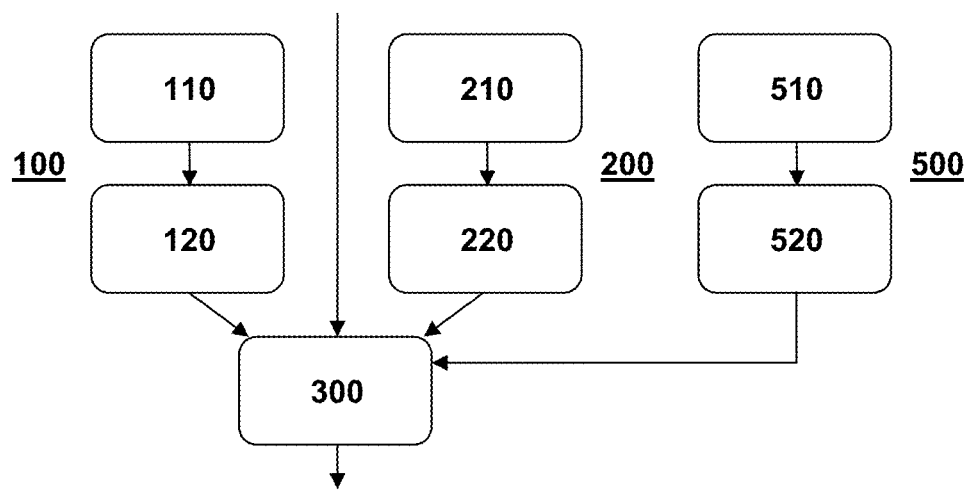
FIG. 5 shows a partial flowchart for performing an embodiment of the present invention with additional steps for receiving third image data.

FIG. 5 shows a partial flowchart for performing an embodiment of the present invention with additional steps for receiving third image data so that data from more than two images can be used to assess a structural defect presence in the structure.

According to an embodiment, the method further comprises a step of obtaining third image data 500. The step 500 of obtaining third image data comprises a step 510 of capturing a third image of the surface of the structure under a third loading condition, and a step 520 of processing the captured third image to obtain the third image data.

Then the third image data is used to average and/or interpolate deformation values for each corresponding correlated region or part of the surface.

So the step 300 of obtaining the deformation matrix, the step 410 of calculating the strain matrix and the step 420 of determining a micro-crack to be present at a position further comprise a step of obtaining a deformation value at each position of the position matrix using an image correlation technique on the third image with at least one of the first or second images. In addition, the step 300 of obtaining the deformation matrix, the step 410 of calculating the strain matrix and the step 420 of determining a micro-crack to be present at a position comprise steps of averaging and/or interpolating from the deformation values and/or strain values obtained/calculated from the first and second image comparison, the first and third image comparison, and/or the second and third image comparison.

According to an embodiment, the third loading condition is the same as the first or second loading condition, and the averaging comprises averaging the deformation values and/ or strain values obtained/calculated from the first or second image under the same loading condition as the third loading condition.

According to another embodiment, the third loading condition is different from the first or second loading condition, and the interpolating comprises interpolating from the deformation values and/or strain values obtained/calculated from the first or second image under the different loading condition than the third loading condition.

By averaging and/or interpolating image data values from more than one captured image this way, an error or undesirable effect introduced to the image data from an anomaly in a captured image may be reduced. It is understood that according to another embodiment, more than three images may be used for a similar benefit.

Figure 6:
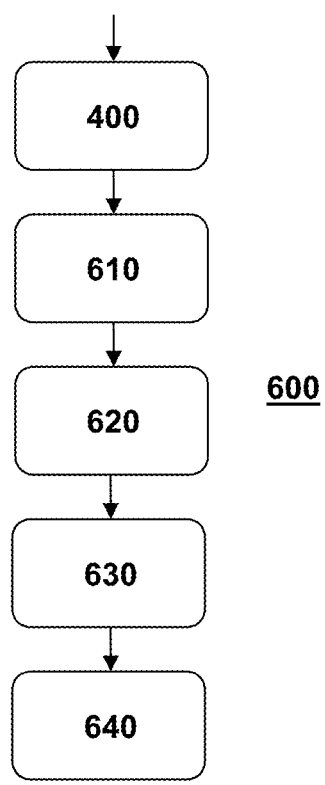
FIG. 6 shows a partial flowchart for performing an embodiment of the present invention with additional steps for determining and/or predicting a crack propagation path.

FIG. 6 shows a partial flowchart for performing an embodiment of the present invention with additional steps for determining and/or predicting a crack propagation path.

According to an embodiment, the method determines/predicts a crack propagation path within the structure and/or the concrete portion of the structure at step 600. The crack propagation path comprises at least two positions which have been determined to have a micro-crack present at step 400. By determining and/or predicting the crack propagation path, the method illustrates progress of a crack path and how it might propagate further as the loading condition changes and/or time passes.

The step 600 of determining and/or predicting a crack propagation path comprises the sub-steps of:

a step 610 of determining a potential damage zone which is a set of all the neighbouring positions determined to have a micro-crack present from step 400;

a step 620 of obtaining a potential damage strain matrix by selecting the elements relating to the potential damage zone from the strain matrix;

a step 630 of determining at least one local maximum strain value for each row and/or column of the potential damage strain matrix if an element therein represents a strain with greater value than both the previous and subsequent elements in the potential damage strain matrix; and a step 640 of determining the crack propagation path to be a collection of positions related to the at least one local maximum strain values.

According to an embodiment, at the step 630, the at least one local maximum strain is determined by comparing the magnitude of an element in a row and/or column of the potential damage strain matrix with the magnitude of a second element that is previous in the row and/or column, and also with the magnitude of a third element that is subsequent to the element in the row and/or column. By selecting the elements with greater value/magnitude than both the previous and subsequent elements in the row and/or column of the potential damage strain matrix, at least one local maximum strain value is determined. Then, the crack propagation path is determined as a collection of positions which are related to the at least one local maximum strain values.

At step 640, the positions related to the at least one local maximum strain values is obtained by selecting the elements relating to the at least one local maximum strain values from the position matrix. So, the collection of the positions is a sub-set of the set of all the neighbouring positions from step 610 which experiences one of the at least one local maximum strain values.

According to an embodiment, the crack propagation path is determined so that it only comprises positions which are related to local maximum strain values, from the determined at least one local maximum strain values, which are next to one another, either in the column-wise and/or row-wise direction of the potential damage strain matrix.

According to an embodiment, the crack propagation path can also comprise more than one collection of the positions related to the at least one local maximum strain values. This enables, potentially, the crack propagation path to comprise more than one pocket of the collection of the positions related to the at least one local maximum strain so that the crack path is not restricted to continuous path only.

According to an embodiment, at the step 640 of determining the crack propagation path, a distribution function for providing a rule for defining the crack path distribution within the determined potential damage zone of the step 610 is used so that the determined crack propagation path adheres to the rule of the distribution function. Preferably, the rule of the distribution function ensures the crack propagation path is a good approximation of a real life crack propagation within a potential damage zone.

According to an embodiment, a distance transform function, say $d((x,y))$, can be used in conjunction with the determined at least one local maximum strain value of step 630. For all the positions in the determined potential damage zone of the step 610, the distance transform function representing the position's shortest distance from the outer boundary of the determined potential damage zone is applied so that the determined crack propagation path continuously connects at least all the positions with the highest distance transform function value, i.e. the positions that are furthest away from the outer boundary of the determined potential damage zone.

It is understood that any other distribution function can be used with the step 640. So any distribution function may be used according to another embodiment of the present invention as long as it can provide a rule for distributing the crack propagation path within the determined potential damage zone. For example, a random distribution function with its local maxima positions closely correlating with the local maximum strain value positions in the potential damage zone may be used.

Figure 7:
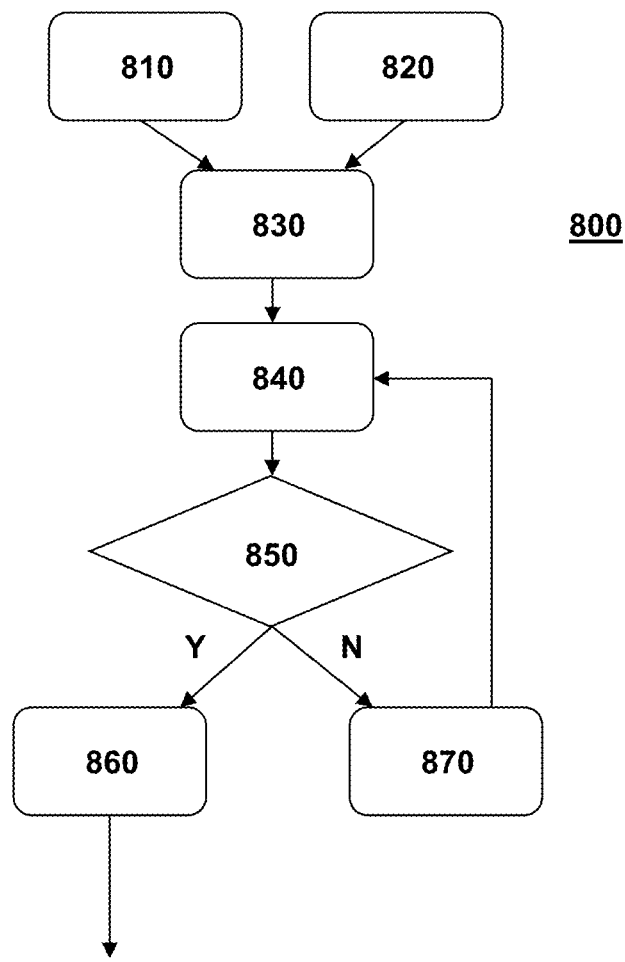
FIG. 7 shows a partial flowchart for performing an embodiment of the present invention with additional steps for determining at least one critical damage strain value.

FIG. 7 shows a partial flowchart for performing an embodiment of the present invention with additional steps for determining at least one critical damage strain value at step 800. The critical damage strain value is a critical strain value at which a structural defect such as a crack is likely to occur.

According to an embodiment, the method comprising the step 400 of determining a position with a micro-crack present therein as discussed above, also comprises the step 800 of determining the at least one critical damage strain value of the structure which comprises the sub-steps of:

a step 810 of capturing a prior image before a detectable macro-crack has occurred;

a step 820 of capturing a post image after the detectable macro-crack has occurred;

a step 830 of setting the critical damage strain value as a first predicted critical strain value;

a step 840 of performing at least some of the rest of the method steps using the prior image as the first image, the post image as the second image and the first predicted critical strain value as the critical damage strain value, to determine whether a micro-crack is present at a position at step 400; and a step 850 of performing the following sub-step at least once until there is an acceptable degree of correlation between the determined position with a micro-crack present and the location of the detectable macro-crack in the post image, wherein if there is an acceptable degree of correlation, as a step 860 saving the first predicted critical strain value as the determined critical damage strain value, and if there is not an acceptable degree of correlation, repeating at least some of the sub-steps for the determining at least one critical damage strain value after, as a step 870 setting a second predicted critical strain value, which is different from the first predicted critical strain value, as the critical damage strain value.

At step 850 of assessing the degree of correlation, the determined position with a micro-crack present and the location of the detectable macro-crack in the second image, i.e. the post image, shows an acceptable degree of correlation if the determined position is near the location of the detectable macro-crack to a predetermined acceptable degree.

According to an embodiment, the method comprising the step 600 of determining and/or predicting a crack propagation path as discussed above, also comprises the step 800 of determining the at least one critical damage strain value of the structure which comprises the sub-steps of:

a step 810 of capturing a prior image before a detectable macro-crack has occurred;

a step 820 of capturing a post image after the detectable macro-crack has occurred;

a step 830 of setting the critical damage strain value as a first predicted critical strain value;

a step 840 of performing at least some of the rest of the method steps using the prior image as the first image, the post image as the second image and the first predicted critical strain value as the critical damage strain value, to determine the crack propagation path at step 600; and a step 850 of performing the following sub-step at least once until there is an acceptable degree of correlation between the determined crack propagation path and the location of the detectable macro-crack in the post image, wherein if there is an acceptable degree of correlation, as a step 860 saving the first predicted critical strain value as the determined critical damage strain value, and if there is not an acceptable degree of correlation, repeating at least some of the sub-steps for the step 800 of determining at least one critical damage strain value after, as a step 870 setting a second predicted critical strain value, which is different from the first predicted critical strain value, as the critical damage strain value.

The at least some of the rest of the method steps in step 840 may be steps 100, 200, 300, and 400 so that whether a micro-crack is present at a position or not can be assessed and/or determined using the image data obtained from the prior and post images. It is understood that any combination and/or partial steps of the method steps may be performed instead as long as the resulting determined position with a micro-crack present enables the comparison step 850 to determine or check whether there is an acceptable degree of correlation between the determined position with a micro-crack present and the location of the detectable macro-crack in the second image, i.e. the post image. It is also understood that a digital image correlation technique similar to that described herein may be used with the step 850 of assessing the degree of correlation.

The at least some of the sub-steps for the determining at least one critical damage strain value described in steps 850 and 870 may be the sub-steps 830, 840 and 850 with the second predicted critical strain value set as the critical damage strain value. It is understood that any combination and/or partial sub-steps of the sub-steps may be performed as long as, after using the second predicted critical strain value as the critical damage strain value, the resulting determined position with a micro-crack present and/or crack propagation path enables the comparison step 850 to determine or check whether there is an acceptable degree of correlation with the detectable macro-crack in the second image, i.e. the post image.

According to an embodiment, at step 850 of assessing the degree of correlation, the determined crack propagation path and the location of the detectable macro-crack in the second image, i.e. the post image, shows an acceptable degree of correlation if the location of the detectable macro-crack is sufficiently near a point in the determined crack propagation path.

For example, there is an acceptable degree of correlation between the determined crack propagation path and the location of the detectable macro-crack in the post image when the determined crack propagation path comprises the location of the detectable macro-crack.

Alternatively, there is an acceptable degree of correlation between the determined crack propagation path and the location of the detectable macro-crack in the post image when the detectable macro-crack is near a periphery of the determined crack propagation path.

Additionally and/or alternatively, there is an acceptable degree of correlation between the determined crack propagation path and the location of the detectable macro-crack in the post image if the potential damage zone determined in step 610 using the set critical damage strain value shows close correlation with the physical damage zone detectable or visible from the post image.

According to an embodiment, when the step 800 is performed for the first time, at the step 830 an arbitrary value is used as the first predicted critical strain value. Alternatively, when the step 800 is performed for the first time, the first predicted critical strain value is obtained by performing a standard material test such as ASTM (American Society for Testing and Materials) tensile test, on a sample which represents the structure and/or a composition material wherefrom the structure is made.

The saved critical damage strain value of the step 860 is used as a threshold value, i.e. the predetermined critical damage strain value of the step 400, for determining a position or location and/or crack propagation path of a micro-crack resulting from the loading on the structure.

According to an embodiment, the second predicted critical strain value of the step 870 is of an arbitrary value. Additionally and/or alternatively, the second predicted critical strain value of the step 870 is obtained by performing a standard material test such as ASTM (American Society for Testing and Materials) tensile test, on a sample which represents the structure and/or a composition material wherefrom the structure is made.

Additionally and/or alternatively, the second predicted critical strain value of the step 870 is obtained by increasing or decreasing the first predicted critical strain value by a predetermined magnitude, for example by a certain percentage. Additionally and/or alternatively, the second predicted critical strain value of the step 870 is extrapolated and/or interpolated from at least two different predicted critical strain values on which step 850 is performed in previous sub-steps of the step 800 of determining the at least one critical damage strain value.

Figure 8A:
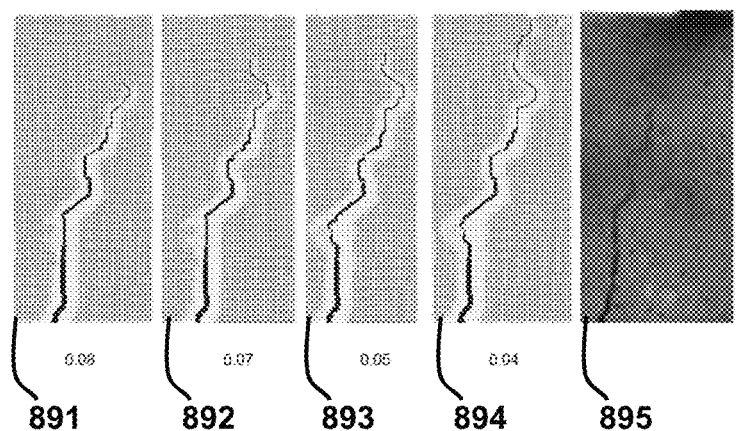
FIG. 8A shows an exemplary crack and determined and/or predicted crack locations and/or propagation paths obtained using different critical damage strain values.

FIG. 8A shows an exemplary crack 895 and determined and/or predicted crack locations and/or propagation paths 891, 892, 893, 894 obtained using different critical damage strain values when the steps 850-870 are repeated. The crack location and/or propagation path 891, 892, 893, and 894 are determined after setting the critical damage strain value to 0.08, 0.07, 0.05, and 0.04 respectively. It can be seen that on this occasion the crack propagation paths 893, 894 determined using smaller critical damage strain values, i.e. 0.05 or 0.04, show better correlation with the exemplary crack 895. So, according to an embodiment of the present invention, the smaller critical values 0.05 or 0.04 are saved as the determined critical damage strain values in step 800/860 so that it can be used in the step 400 to determine whether there is a micro-crack present at a position, i.e. to determine a crack location as the location with a detected micro-crack.

Figure 8B:
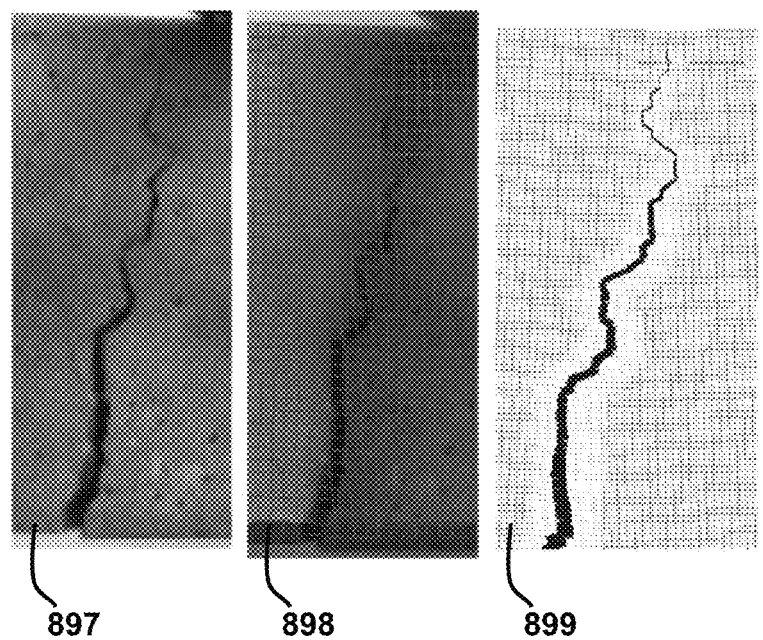
FIG. 8B shows a comparison between an exemplary crack and a determined and/or predicted crack location and/or propagation path obtained using a determined critical damage strain value.

FIG. 8B shows a comparison between an exemplary crack 897, a grid or coordinate system 898 showing deformation of the exemplary crack, and a determined and/or predicted crack location and/or propagation path 899 obtained using a determined critical damage strain value according to an embodiment of the present invention. It can be seen that there is a good agreement, i.e. correlation, between the determined and/or predicted crack location and/or propagation path 899 and the actual exemplary crack 897. Even each bend/curvature of the exemplary crack 897 is well determined and/or predicted by the embodiment.

Figure 9:
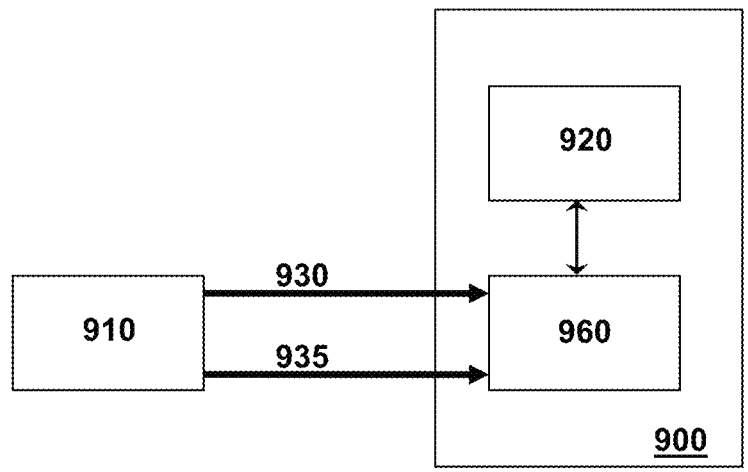
FIG. 9 shows an assessment apparatus embodiment of the present invention in communication with an exemplary image data provider.

FIG. 9 shows an assessment apparatus 900 according to an embodiment of the present invention. The assessment apparatus 90 is in communication with an exemplary image data provider. An example of such an image data provider is an image capturing unit 910 which captures and/or stores images of the surface of the structure.

The assessment apparatus 900 for assessing a structural defect presence in a structure comprises:

a communication unit 960 for receiving first data 930 relating to a first image of a surface of the structure under a first loading condition, and receiving second data 935 relating to a second image of the surface of the structure under a second loading condition; and a processor 920 for:

determining at least one critical damage strain value of the structure;

assigning a position matrix on the captured first image;

obtaining a deformation matrix comprising a deformation value at each position of the position matrix by using an image correlation technique on the first and second images, and by comparing deformation of corresponding parts of the surface captured therein;

calculating a strain matrix using the obtained deformation matrix; and determining a micro-crack to be present at a position if an element of the strain matrix representing the strain at the position is greater than or equal to a predetermined critical damage strain value, wherein the critical damage strain value is a strain value at which a micro-crack is detected or predicted to appear and/or propagate.

The communication unit 960 receives the first and/or second data 930, 935 from the image capturing unit 910 using a wired and/or wireless communication. The assessment apparatus 900 and/or the processor 920 also operates and/or performs any of the methods and/or method steps described herein to assess the structural defect presence in the structure.

Figure 10:
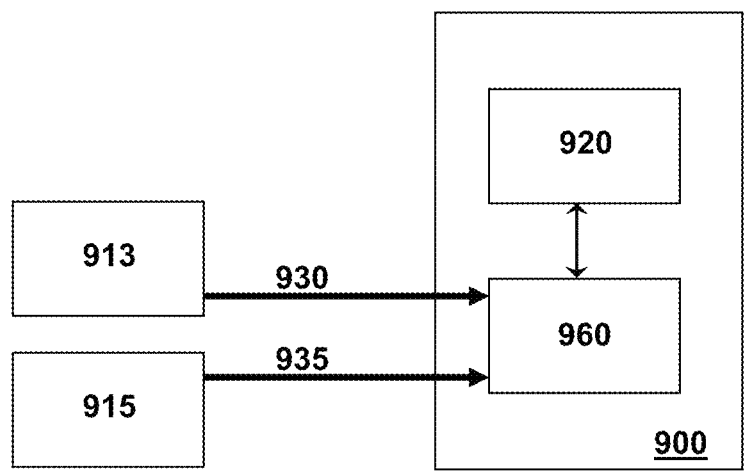
FIG. 10 shows an assessment apparatus embodiment of the present invention in communication with an alternative image data provider to the one shown in FIG. 9.

FIG. 10 shows the assessment apparatus 900 of FIG. 9 in communication with an alternative image data provider to the one shown in FIG. 8. The image data provider comprises a first image capturing unit 913 which captures and/or stores the first image of the surface of the structure, and a second image capturing unit 915 which captures and/or stores the second image of the surface of the structure. The communication unit 960 of the assessment apparatus 900 receives the first data 930 from the first image capturing unit 913 and the second data 935 from the second image capturing unit 915.

It is understood that where more than two images are used in accordance with an embodiment of the present invention, more than two image capturing units may be in communication with the communication unit 960 to send the image data there-from.

Figure 11:
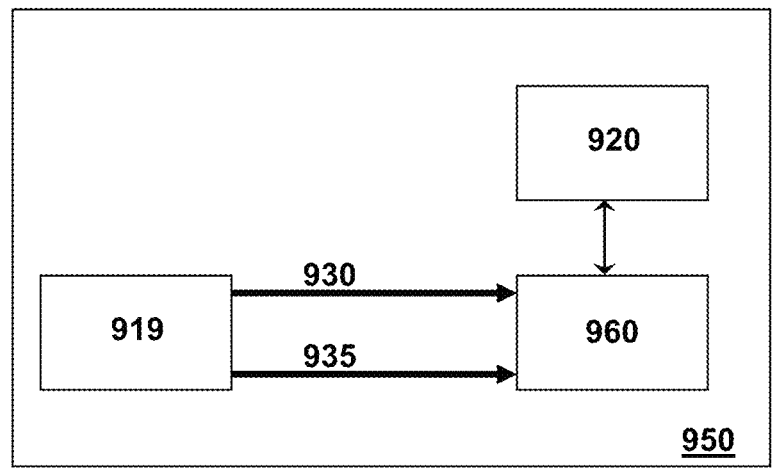
FIG. 11 shows an alternative assessment apparatus embodiment of the present invention.

FIG. 11 shows an alternative assessment apparatus 950 which comprises an image data provider, i.e. an image capturing unit 919. The image capturing unit 919 captures and/or stores the first data 930 and the second data 935 which is then provided to the processor 920 for processing of the first and second data 930, 935. It is understood that in FIG. 11 the communication unit 960 may merely be a communication channel, both wired and wireless, or a bus for transferring the first and second data 930, 935 from the image capturing unit 919 to the processor 920.

According to an embodiment, the image capturing unit 910, 913, 915, 919 captures the first image of at least a portion of the surface of the structure under the first loading condition, and captures the second image of the at least the portion of the surface of the structure under the second loading condition.

According to an embodiment, the image capturing unit 910, 913, 915, 919 captures the second image at a different time from the time of capturing the first image.

The image capturing unit 910, 913, 915, 919 may also capture a plurality of images over a period of time, for example a moving picture, whereby data relating to the plurality of images is obtained. The processor 920 is then able to obtain the deformation matrix using the plurality of images.

According to an embodiment, there is provided a computer readable medium storing a computer program to operate the method according to the embodiments described herein.

Figure 12:
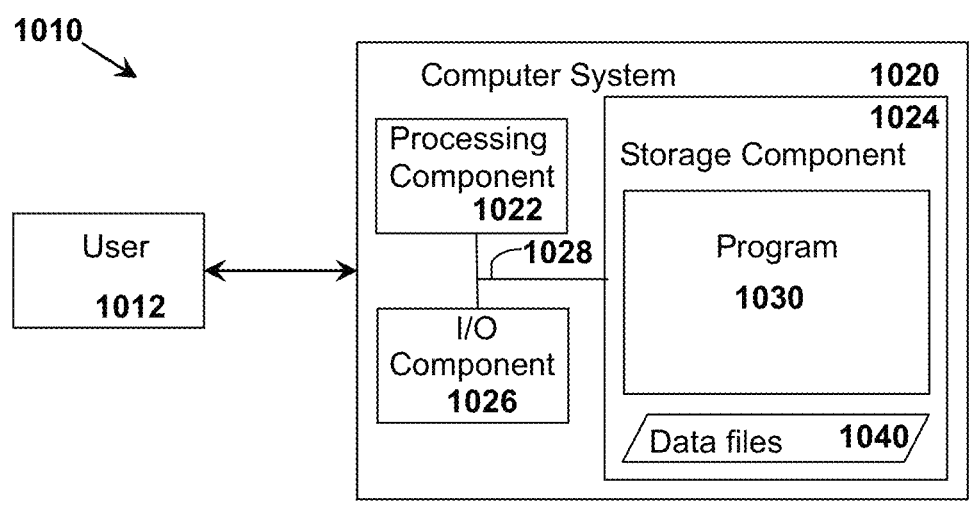
FIG. 12 shows an illustrative environment according to an embodiment of the present invention.

FIG. 12 shows an illustrative environment 1010 according to an embodiment of the invention. The skilled person will realise and understand that embodiments of the present invention may be implemented using any suitable computer system, and the example system shown in FIG. 12 is exemplary only and provided for the purposes of completeness only. To this extent, environment 1010 includes a computer system 1020 that can perform a process described herein in order to perform an embodiment of the invention. In particular, computer system 1020 is shown including a program 1030, which makes computer system 1020 operable to implement an embodiment of the invention by performing a process described herein.

Computer system 1020 is shown including a processing component 1022 (e.g., one or more processors), a storage component 1024 (e.g., a storage hierarchy), an input/output (I/O) component 1026 (e.g., one or more I/O interfaces and/or devices), and a communications pathway 1028. In general, processing component 1022 executes program code, such as program 1030, which is at least partially fixed in storage component 1024. While executing program code, processing component 1022 can process data, which can result in reading and/or writing transformed data from/to storage component 1024 and/or I/O component 1026 for further processing. Pathway 1028 provides a communications link between each of the components in computer system 1020. I/O component 1026 can comprise one or more human I/O devices, which enable a human user 1012 to interact with computer system 1020 and/or one or more communications devices to enable a system user 1012 to communicate with computer system 1020 using any type of communications link. To this extent, program 1030 can manage a set of interfaces (e.g., graphical user interface(s), application program interface, and/or the like) that enable human and/or system users 1012 to interact with program 1030. Further, program 1030 can manage (e.g., store, retrieve, create, manipulate, organize, present, etc.) the data, such as a plurality of data files 1040, using any solution.

In any event, computer system 1020 can comprise one or more general purpose computing articles of manufacture (e.g., computing devices) capable of executing program code, such as program 1030, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, program 1030 can be embodied as any combination of system software and/or application software.

Further, program 1030 can be implemented using a set of modules. In this case, a module can enable computer system 1020 to perform a set of tasks used by program 1030, and can be separately developed and/or implemented apart from other portions of program 1030. As used herein, the term "component" means any configuration of hardware, with or without software, which implements the functionality described in conjunction therewith using any solution, while the term "module" means program code that enables a computer system 1020 to implement the actions described in conjunction therewith using any solution. When fixed in a storage component 1024 of a computer system 1020 that includes a processing component 1022, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computer system 1020.

When computer system 1020 comprises multiple computing devices, each computing device can have only a portion of program 1030 fixed thereon (e.g., one or more modules). However, it is understood that computer system 1020 and program 1030 are only representative of various possible equivalent computer systems that may perform a process described herein. To this extent, in other embodiments, the functionality provided by computer system 1020 and program 1030 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 1020 includes multiple computing devices, the computing devices can communicate over any type of communications link. Further, while performing a process described herein, computer system 1020 can communicate with one or more other computer systems using any type of communications link. In either case, the communications link can comprise any combination of various types of optical fibre, wired, and/or wireless links; comprise any combination of one or more types of networks; and/or utilize any combination of various types of transmission techniques and protocols.

In any event, computer system 1020 can obtain data from files 1040 using any solution. For example, computer system 1020 can generate and/or be used to generate data files 1040, retrieve data from files 1040, which may be stored in one or more data stores, receive data from files 1040 from another system, and/or the like.

It is understood that a matrix can refer to any set or collection of at least one element. For example, a position matrix may be a mere set or collection of a plurality of positions which are assigned to a particular location or part of a surface. It is also understood that the assignment of the position to the location or part of the surface may be in a grid or in any random fashion as long as each location or part can be identified with the position.

It is understood that if a potentially significant structural instability is predicted from the determined micro-crack at step 400 and/or the crack propagation path at step 600 according to any one of the embodiments of the present invention, an action is taken to notify a user of the predicted structural instability and/or treat the affected region of the structure. For example, the action may be issuing a warning to a user. The action may further comprise mechanically reinforcing the potential damage zone of step 610 and/or regions around the potential damage zone to improve structural stability. Alternatively, the action may comprise removing, repairing and/or replacing the structure, concrete portion and/or a region of the structure causing the structural instability.

By detecting and/or predicting potentially fatal structural defects such as micro-cracks and taking an action to treat the affected region, further propagation and/or development of the structural defects eventually leading to a structural instability and/or danger is prevented before they reach an irreversible degree, for example through development into a macro-crack. The present invention predicts potential locations and/or propagation of the macro-cracks by detecting the locations and/or propagation of the micro-cracks through modelling thereof. This then enables notification and/or treatment, such as providing additional concrete layer and/or reinforcement, of the structure before it suffers the irreversible/significant damage/structural defect. Also, this enables determination of whether the structure is still capable of dealing with the normal use loading condition and/or for how long the structure might remain safe to be used in the normal use loading condition. This determination then enables a repair, replacement and/or removal of the structure, and/or adjustment of the normal use loading condition, to be performed as appropriate.

According to an embodiment, if a micro-crack is determined to be present at a particular position at step 400 and/or a crack propagation path is determined to extend over a threshold length at step 640, the method and/or apparatus assesses there to be a potentially significant structural instability. According to an embodiment, the particular position is a location with a mechanical weakness and/or the threshold length is predetermined through an experiment on a sample.

It is understood that according to an embodiment of the present invention, a plurality of images are captured over a period of time so that the method and/or apparatus of the present invention is used on the plurality of the captured images to assess, detect, determine, and/or predict how a position of a crack location and/or a crack propagation path might progress in the future. Then, this assessment, detection, determination, and/or prediction is used to notify a user, and/or treat, remove, repair, and/or replace the affected region or part of the structure, and/or to adjust the normal use loading conditions of the structure as appropriate, whereby potentially detrimental or significant structural instability in the future is avoided.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of assessing a structural defect presence in a structure, the method comprising:
    capturing a first image of a surface of the structure under a first loading condition;
    capturing a second image of the surface of the structure under a second loading condition;
    assigning a position matrix on the captured first image;
    obtaining a deformation matrix comprising a deformation value at each position of the position matrix by using an image correlation technique on the first and second images, and by comparing deformation of corresponding parts of the surface captured therein;
    calculating a strain matrix using the obtained deformation matrix;
    determining a micro-crack to be present at a position if an element of the strain matrix representing the strain at the position is greater than or equal to a predetermined critical damage strain value, wherein the predetermined critical damage strain value is a strain value at which a micro-crack is detected or predicted to appear and/or propagate; and
    determining and/or detecting a crack propagation path, the determining and/or detecting comprising
        determining a potential damage zone which is a set of all neighbouring positions determined to have a micro-crack present,
        obtaining a potential damage strain matrix by selecting the elements relating to the potential damage zone from the strain matrix,
        determining at least one local maximum strain value for each row and/or column of the potential damage strain matrix if an element therein represents a strain with greater value than both the previous and subsequent elements in the potential damage strain matrix, and
        determining the crack propagation path to be a collection of positions related to the at least one local maximum strain values.

2. The method of claim 1, wherein the structure comprises a concrete portion.

3. The method of claim 1, further comprising capturing a third image of the surface of the structure under a third loading condition, wherein obtaining the deformation matrix, calculating the strain matrix, and determining a micro-crack to be present at a position comprise obtaining a deformation value at each position of the position matrix using an image correlation technique on the third image with at least one of the first or second images.

4. The method of claim 3, further comprising applying or affixing an indicator on a part of the surface so that the indicator is detectable from one or more of the captured first image, second image, or third image, whereby the part can be identified in the first, second, or third image using the indicator.

5. The method of claim 1, wherein the positions related to the at least one local maximum strain values is obtained by selecting the elements relating to the at least one local maximum strain values from the position matrix.

6. The method of claim 1, wherein the crack propagation path comprises a collection of the positions related to the at least one local maximum strain values which only comprises positions related to local maximum strain values which are next to one another, either in the column-wise and/or row-wise direction of the potential damage strain matrix.

7. The method of claim 1, wherein prior to assigning a position matrix on the captured first image, the method further comprises determining at least one critical damage strain value of the structure, wherein determining at least one critical damage strain value of the structure includes:
    capturing a prior image before a detectable macro-crack has occurred;
    capturing a post image after the detectable macro-crack has occurred;
    setting the predetermined critical damage strain value as a first predicted critical strain value; and
    performing at least the assigning, the obtaining a deformation matrix, the calculating, and the determining a micro-crack using the prior image as the first image, the post image as the second image, and the first predicted critical strain value as the predetermined critical damage strain value, to determine a position with a micro-crack present;
    wherein if there is an acceptable degree of correlation between the determined position and the location of the detectable macro-crack in the post image, saving the first predicted critical strain value as the predetermined critical damage strain value, and
    wherein if there is not an acceptable degree of correlation between the determined position and the location of the detectable macro-crack in the post image, setting the predetermined critical damage strain value as a next predicted critical strain value, which is different from the first predicted critical strain value, and repeat performing at least the assigning, the obtaining a deformation matrix, the calculating, and the determining a micro-crack using the prior image as the first image, the post image as the second image, and the next predicted critical strain value as the predetermined critical damage strain value, to determine a position with a micro-crack present.

8. The method of claim 1, wherein prior to assigning a position matrix on the captured first image, the method further comprises determining at least one critical damage strain value of the structure, wherein determining at least one critical damage strain value of the structure includes:
capturing a prior image before a detectable macro-crack has occurred;
capturing a post image after the detectable macro-crack has occurred;
setting the predetermined critical damage strain value as a first predicted critical strain value; and
performing at least the assigning, the obtaining a deformation matrix, the calculating, the determining a micro-crack, and the determining and/or detecting a crack propagation path using the prior image as the first image, the post image as the second image, and the first predicted critical strain value as the predetermined critical damage strain value, to determine the crack propagation path;
wherein if there is an acceptable degree of correlation between the determined crack propagation path and the location of the detectable macro-crack in the post image, saving the first predicted critical strain value as the predetermined critical damage strain value, and
wherein if there is not an acceptable degree of correlation between the determined crack propagation path and the location of the detectable macro-crack in the post image, setting the predetermined critical damage strain value as a next predicted critical strain value, which is different from the first predicted critical strain value, and repeat performing the assigning, the obtaining a deformation matrix, the calculating, the determining a micro-crack, and the determining and/or detecting a crack propagation path using the prior image as the first image, the post image as the second image, and the next predicted critical strain value as the predetermined critical damage strain value, to determine the crack propagation path.

9. The method of claim 8, wherein there is an acceptable degree of correlation between the determined crack propagation path and the location of the detectable macro-crack in the post or second image when the detectable macro-crack is near a periphery of the determined crack propagation path.

10. An assessment apparatus for assessing a structural defect presence in a structure, the apparatus comprising:
a communication unit configured to receive first data relating to a first image of a surface of the structure under a first loading condition, and to receive second data relating to a second image of the surface of the structure under a second loading condition; and
a processor configured to:
assign a position matrix on the captured first image;
obtain a deformation matrix comprising a deformation value at each position of the position matrix by using an image correlation technique on the first and second images, and by comparing deformation of corresponding parts of the surface captured therein;
calculate a strain matrix using the obtained deformation matrix;
determine a micro-crack to be present at a position if an element of the strain matrix representing the strain at the position is greater than or equal to a predetermined critical damage strain value, wherein the predetermined critical damage strain value is a strain value at which a micro-crack is detected or predicted to appear and/or propagate;
determine a potential damage zone which is a set of all neighbouring positions determined to have a micro-crack present;
obtain a potential damage strain matrix by selecting the elements relating to the potential damage zone from the strain matrix;
determine at least one local maximum strain value for each row and/or column of the potential damage strain matrix if an element therein represents a strain with greater value than both the previous and subsequent elements in the potential damage strain matrix; and
determine a crack propagation path to be a collection of positions related to the at least one local maximum strain values.

11. The assessment apparatus of claim 10, further comprising an image capturing unit configured to capture the first image of at least a portion of the surface of the structure under the first loading condition, and to capture the second image of the at least the portion of the surface of the structure under the second loading condition.

12. The assessment apparatus of claim 11, wherein the image capturing unit is configured to capture a plurality of images over a period of time, whereby data relating to a plurality of images is obtained and the processor is configured to obtain the deformation matrix using the plurality of images.

13. The assessment apparatus of claim 10, wherein the processor is further configured to determine at least one critical damage strain value of the structure, such that the processor is configured to:
cause capture of a prior image before a detectable macro-crack has occurred;
cause capture of a post image after the detectable macro-crack has occurred;
set the predetermined critical damage strain value as a first predicted critical strain value; and
use the prior image as the first image, the post image as the second image, and the first predicted critical strain value as the predetermined critical damage strain value, to determine the crack propagation path;
wherein if there is an acceptable degree of correlation between the determined crack propagation path and the location of the detectable macro-crack in the post image, the processor is further configured to save the first predicted critical strain value as the predetermined critical damage strain value, and
wherein if there is not an acceptable degree of correlation between the determined crack propagation path and the location of the detectable macro-crack in the post image, the processor is further configured to set the predetermined critical damage strain value as a next predicted critical strain value, which is different from the first predicted critical strain value, and use the prior image as the first image, the post image as the second image, and the next predicted critical strain value as the predetermined critical damage strain value, to determine the crack propagation path.

14. A computer program product including one or more non-transitory computer readable mediums encoded with instructions that when executed by one or more processors cause a process to be carried out for assessing a structural defect presence in a structure, the process comprising:
receive first data relating to a first image of a surface of the structure under a first loading condition, and receive second data relating to a second image of the surface of the structure under a second loading condition;

assign a position matrix on the captured first image;

obtain a deformation matrix comprising a deformation value at each position of the position matrix by using an image correlation technique on the first and second images, and by comparing deformation of corresponding parts of the surface captured therein;

calculate a strain matrix using the obtained deformation matrix;

determine a micro-crack to be present at a position if an element of the strain matrix representing the strain at the position is greater than or equal to a predetermined critical damage strain value, wherein the predetermined critical damage strain value is a strain value at which a micro-crack is detected or predicted to appear and/or propagate;

determine a potential damage zone which is a set of all neighbouring positions determined to have a micro-crack present;

obtain a potential damage strain matrix by selecting the elements relating to the potential damage zone from the strain matrix;

determine at least one local maximum strain value for each row and/or column of the potential damage strain matrix if an element therein represents a strain with greater value than both the previous and subsequent elements in the potential damage strain matrix; and determine a crack propagation path to be a collection of positions related to the at least one local maximum strain values.

15. The computer program product of claim 14, wherein the processor receives data relating to a plurality of images over a period of time, whereby data relating to a plurality of images is obtained, and the deformation matrix is obtained using the plurality of images.

16. The computer program product of claim 14, wherein the process further includes determine at least one critical damage strain value of the structure, such that the process is configured to:

cause capture of a prior image before a detectable macro-crack has occurred;

cause capture of a post image after the detectable macro-crack has occurred;

set the predetermined critical damage strain value as a first predicted critical strain value; and use the prior image as the first image, the post image as the second image, and the first predicted critical strain value as the predetermined critical damage strain value, to determine the crack propagation path;

wherein if there is an acceptable degree of correlation between the determined crack propagation path and the location of the detectable macro-crack in the post image, the processor is further configured to save the first predicted critical strain value as the predetermined critical damage strain value, and wherein if there is not an acceptable degree of correlation between the determined crack propagation path and the location of the detectable macro-crack in the post image, the processor is further configured to set the predetermined critical damage strain value as a next predicted critical strain value, which is different from the first predicted critical strain value, and use the prior image as the first image, the post image as the second image, and the next predicted critical strain value as the predetermined critical damage strain value, to determine the crack propagation path.

17. The computer program product of claim 14, the process further comprising cause capture of a third image of the surface of the structure under a third loading condition, wherein a least one of obtaining the deformation matrix, calculating the strain matrix, and determining a micro-crack to be present at a position include obtain a deformation value at each position of the position matrix using an image correlation technique on the third image with at least one of the first or second images.

18. The computer program product of claim 14, wherein the positions related to the at least one local maximum strain values is obtained by selecting the elements relating to the at least one local maximum strain values from the position matrix, and/or wherein the crack propagation path comprises a collection of the positions related to the at least one local maximum strain values which only comprises positions related to local maximum strain values which are next to one another, either in the column-wise and/or row-wise direction of the potential damage strain matrix.

\* \* \* \* \*